(12) United States Patent
Iwane

(10) Patent No.: US 9,794,494 B2
(45) Date of Patent: Oct. 17, 2017

(54) ENDOSCOPE SYSTEM AND METHOD WITH PIXEL GAIN CORRECTION

(71) Applicant: FUJIFILM Corporation, Tokyo (JP)

(72) Inventor: Kosuke Iwane, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 249 days.

(21) Appl. No.: 14/497,941

(22) Filed: Sep. 26, 2014

(65) Prior Publication Data
US 2015/0092034 A1  Apr. 2, 2015

(30) Foreign Application Priority Data
Sep. 27, 2013  (JP) ................. 2013-201501

(51) Int. Cl.
| H04N 7/18 | (2006.01) |
|---|---|
| H04N 5/243 | (2006.01) |
| A61B 1/00 | (2006.01) |
| A61B 1/06 | (2006.01) |
| A61B 1/045 | (2006.01) |

(Continued)

(52) U.S. Cl.
CPC ......... *H04N 5/243* (2013.01); *A61B 1/00009* (2013.01); *A61B 1/00057* (2013.01); *A61B 1/045* (2013.01); *A61B 1/0638* (2013.01); *H04N 9/045* (2013.01); *H04N 2005/2255* (2013.01)

(58) Field of Classification Search
CPC ....................................... H04N 5/243
USPC ........................................... 348/68
See application file for complete search history.

(56) References Cited

U.S. PATENT DOCUMENTS

2007/0102623 A1* 5/2007 Fengler .............. A61B 1/00009
                                                    250/208.1
2009/0118578 A1   5/2009 Takasugi et al.
(Continued)

FOREIGN PATENT DOCUMENTS

| EP | 1 698 271 A1 | 9/2006 |
|---|---|---|
| EP | 1 994 875 A1 | 11/2008 |

(Continued)

OTHER PUBLICATIONS

Extended European Search Report dated Mar. 23, 2015, issued in corresponding European Patent Application No. 14186508.9.
(Continued)

*Primary Examiner* — Richard Torrente
(74) *Attorney, Agent, or Firm* — Birch, Stewart, Kolasch & Birch, LLP

(57) ABSTRACT

An endoscope system includes a light source apparatus for emitting narrow band light of green and violet in field sequential lighting, for endoscopic imaging. An image sensor has multiple pixels arranged on an imaging surface, for imaging an object in a body cavity illuminated with the narrow band light, to output a pixel signal. The multiple pixels include first and second pixels. The first pixel has a lower spectral sensitivity than the second pixel. A gain corrector is supplied with the pixel signal by the image sensor, for performing gain correction of multiplying the pixel signal of the first pixel by a gain value, so as to compensate for a difference in the spectral sensitivity of the first pixel from the second pixel. Also, a noise reduction device performs noise reduction of the pixel signal after the gain correction according to the gain value.

14 Claims, 13 Drawing Sheets

(51) Int. Cl.
    *H04N 9/04*     (2006.01)
    *H04N 5/225*    (2006.01)

(56) References Cited

U.S. PATENT DOCUMENTS

| | | | |
|---|---|---|---|
| 2012/0092473 A1* | 4/2012 | Takamatsu | A61B 1/00009 348/74 |
| 2012/0242874 A1* | 9/2012 | Noudo | H01L 27/1464 348/294 |
| 2012/0288194 A1* | 11/2012 | Nakamura | H04N 1/4092 382/167 |
| 2013/0006109 A1 | 1/2013 | Takei et al. | |
| 2013/0076939 A1* | 3/2013 | Kaizu | H04N 9/045 348/224.1 |
| 2013/0222562 A1 | 8/2013 | Ono | |
| 2014/0086505 A1* | 3/2014 | Kim | H04N 5/23229 382/255 |
| 2015/0342448 A1* | 12/2015 | Asatori | G02B 23/2469 600/109 |

FOREIGN PATENT DOCUMENTS

| | | |
|---|---|---|
| JP | 2009-284931 A | 12/2009 |
| JP | 2009-284959 A | 12/2009 |
| WO | WO 2012/140970 A1 | 10/2012 |

OTHER PUBLICATIONS

Japanese Notification of Reasons for Refusal dated Sep. 24, 2015, for Japanese Application No. 2013-201501 with the English translation.

* cited by examiner

FIG. 15

| $P_{1M}$ | $P_{1G} \times K_{1G}$ | $P_{1M}$ | $P_{1G} \times K_{1G}$ |
|---|---|---|---|
| $P_{1C} \times K_{1C}$ | $P_{1Y} \times K_{1Y}$ | $P_{1C} \times K_{1C}$ | $P_{1Y} \times K_{1Y}$ |
| $P_{1M}$ | $P_{1G} \times K_{1G}$ | $P_{1M}$ | $P_{1G} \times K_{1G}$ |
| $P_{1Y} \times K_{1Y}$ | $P_{1C} \times K_{1C}$ | $P_{1Y} \times K_{1Y}$ | $P_{1C} \times K_{1C}$ |

FIG. 16

| $P_{2M}$ | $P_{2G} \times K_{2G}$ | $P_{2M}$ | $P_{2G} \times K_{2G}$ |
|---|---|---|---|
| $P_{2C} \times K_{2C}$ | $P_{2Y} \times K_{2Y}$ | $P_{2C} \times K_{2C}$ | $P_{2Y} \times K_{2Y}$ |
| $P_{2M}$ | $P_{2G} \times K_{2G}$ | $P_{2M}$ | $P_{2G} \times K_{2G}$ |
| $P_{2Y} \times K_{2Y}$ | $P_{2C} \times K_{2C}$ | $P_{2Y} \times K_{2Y}$ | $P_{2C} \times K_{2C}$ |

FIG. 17

| $Q_{1M}$ $Q_{2M}$ | $Q_{1G}$ $Q_{2G}$ | $Q_{1M}$ $Q_{2M}$ | $Q_{1G}$ $Q_{2G}$ |
|---|---|---|---|
| $Q_{1C}$ $Q_{2C}$ | $Q_{1Y}$ $Q_{2Y}$ | $Q_{1C}$ $Q_{2C}$ | $Q_{1Y}$ $Q_{2Y}$ |
| $Q_{1M}$ $Q_{2M}$ | $Q_{1G}$ $Q_{2G}$ | $Q_{1M}$ $Q_{2M}$ | $Q_{1G}$ $Q_{2G}$ |
| $Q_{1Y}$ $Q_{2Y}$ | $Q_{1C}$ $Q_{2C}$ | $Q_{1Y}$ $Q_{2Y}$ | $Q_{1C}$ $Q_{2C}$ |

ENDOSCOPE SYSTEM AND METHOD WITH PIXEL GAIN CORRECTION

CROSS-REFERENCE TO RELATED APPLICATION

This application claims priority under 35 USC 119 from Japanese Patent Application No. 2013-201501, filed 27 Sep. 2013, the disclosure of which is incorporated by reference herein.

BACKGROUND OF THE INVENTION

1. Field of the Invention

The present invention relates to an endoscope system and endoscope operating method. More particularly, the present invention relates to an endoscope system and endoscope operating method in which pixels of an image sensor are corrected by gain correction, and a difference in spectral sensitivity between pixels can be compensated for easily and appropriately.

2. Description Related to the Prior Art

An endoscope system is well-known in the field of medical diagnosis, and includes a light source apparatus, an electronic endoscope and a processing apparatus. The light source apparatus emits light for illumination to an object of interest in a body cavity. An image sensor in the endoscope images the object of interest illuminated with the light, and generates an image signal. The processing apparatus processes the image signal in image processing, and generates an image for display on a monitor display panel.

Two lighting controls are available in the endoscope system, including field sequential lighting and simultaneous lighting. In the field sequential lighting, red (R), green (G) and blue (B) light components are applied to the object of interest sequentially one after another. A monochromatic image sensor images the object of interest illuminated with the light components in sequential steps. In the simultaneous lighting, red (R), green (G) and blue (B) light components are applied to the object of interest simultaneously, so that white light is applied thereto. A multi-color image sensor for use with simultaneous lighting is used, has a color filter, and images the object of interest illuminated with the white light.

The field sequential lighting generates one image by imaging of three frames with the monochromatic image sensor, and has a feature of high spatial resolution and low time resolution. In contrast, the simultaneous lighting generates one image by imaging of one frame with the multi-color image sensor, and has a feature of high time resolution and low spatial resolution. In short, the field sequential lighting and the simultaneous lighting have the features distinct from one another. There is a known endoscope system in which a first endoscope and a second endoscope are selectively connectable to a light source apparatus and a processing apparatus, the first endoscope having the monochromatic image sensor in combination with the field sequential lighting, the second endoscope having the multi-color image sensor in combination with the simultaneous lighting.

It is necessary in an endoscope system to prepare the first and second endoscope. JP-A 2009-284931 and JP-A 2009-284959 suggest a structure in which a lighting control is changeable over between simultaneous lighting and field sequential lighting while the second endoscope is kept connected. In the patent documents, gain correction is performed for a pixel signal of a pixel of a low sensitivity for the light of the plural colors in the pixel signals generated by a multi-color image sensor (for use with simultaneous lighting) in a state of the field sequential lighting for the lighting control. The pixel signal of the pixel of he low sensitivity is used for generating an image together with a pixel signal of a pixel of a high sensitivity, so that spatial resolution can be increased.

A gain value for use in the gain correction is determined by test imaging of a white object with the multi-color image sensor in the field sequential lighting, and by adjusting the white balance in such a manner that a sum of pixel signals of one pixel obtained by lighting of red, green and blue light becomes a value of a pixel signal of white. To be precise, a ratio of a value of pixel signal obtained with first light component of highest sensitivity to a value of pixel signal obtained with remaining light components is obtained in relation to the red, green and blue light components is obtained for each one of pixels of the multi-color image sensor. Then the gain value is determined by obtaining the ratio. For example, the ratio is that of a pixel signal of a red pixel according to lighting with red light to a pixel signal of a red pixel according to lighting with green or blue light.

In general, the pixel signal P is proportional to a value of integration of a product of multiplication of a spectrum $I(\lambda)$ of light intensity of light of illumination, a spectrum $S(\lambda)$ of spectral sensitivity of a pixel, and a spectrum $R(\lambda)$ of spectral reflection of body tissue, from minimum wavelength $\lambda min$ to maximum wavelength $\lambda max$ of the spectrum $I(\lambda)$ of the light intensity. See the mathematical relationship (1).

$$P \propto \int_{\lambda_{min}}^{\lambda_{max}} I(\lambda) \cdot S(\lambda) \cdot R(\lambda) d\lambda \tag{1}$$

In the endoscope system of JP-A 2009-284931 and JP-A 2009-284959, the gain value is determined by obtaining a ratio between values of pixel signals between plural light components with a difference in the wavelength range. Spectral reflectance of body tissue on which values of the pixel signals are dependent is different between the wavelength ranges of the light components. The differences in the spectral reflectance between the wavelength ranges differ between plural samples of the body tissue. See FIG. 14. The gain value must be determined again at each time that the body tissue of imaging is changed.

In the endoscope system of those patent documents, a width of the wavelength range of each one light components (difference between $\lambda max$ and $\lambda min$) is considerably large. Dependency of the spectral reflectance of body tissue or object or interest to the wavelength is not negligible within the wavelength range of the light components. Pixel signals are influenced by the spectral reflectance of the body tissue. It is still necessary to redetermine the gain value for body tissue due to the additional reason.

SUMMARY OF THE INVENTION

In view of the foregoing problems, an object of the present invention is to provide an endoscope system and endoscope operating method in which pixels of an image sensor are corrected by gain correction, and a difference in spectral sensitivity between pixels can be compensated for easily and appropriately.

Another object of the present invention is to provide an endoscope system and endoscope operating method in which gain values of the gain correction for correcting pixels of an image sensor can be obtained with efficiency and simplicity.

In order to achieve the above and other objects and advantages of this invention, an endoscope system includes a light source apparatus for emitting narrow band light of one or more components in field sequential lighting, for endoscopic imaging. An image sensor has plural pixels arranged on an imaging surface, for imaging an object in a body cavity illuminated with the narrow band light, to output a pixel signal, wherein the plural pixels include first and second pixels, and the first pixel has a lower spectral sensitivity than the second pixel. A gain corrector is supplied with the pixel signal by the image sensor, for performing gain correction of multiplying the pixel signal of the first pixel by a gain value, so as to compensate for a difference in the spectral sensitivity of the first pixel from the second pixel.

Preferably, a wavelength range of the narrow band light has a width equal to or less than 30 nm.

Preferably, the gain value is determined according to a spectrum of light intensity of the narrow band light and a spectrum of spectral sensitivity of the first pixel.

Preferably, furthermore, a noise reduction device performs noise reduction of the pixel signal after the gain correction according to the gain value.

Preferably, the noise reduction device obtains an arithmetic mean of the pixel signal of a plurality of frames formed with a time difference to perform the noise reduction, and increases a frame number of the frames for use in obtaining the arithmetic mean according to highness of the gain value.

In another preferred embodiment, the noise reduction device obtains an arithmetic mean of the pixel signal included in image data of one frame to perform the noise reduction, and increases a signal number of the pixel signal for use in obtaining the arithmetic mean according to highness of the gain value.

Preferably, furthermore, a synchronizing circuit synchronizes the pixel signal after the gain correction, to produce image data.

Preferably, the narrow band light is narrow band violet light and narrow band green light.

Preferably, the image sensor includes color filter segments of cyan, magenta, yellow and green colors disposed on the imaging surface, and the pixels are pixels of the cyan, magenta, yellow and green colors.

Preferably, the first pixel is pixels of the cyan, yellow and green colors in imaging by using the narrow band violet light, and is pixels of the cyan, magenta and green colors in imaging by using the narrow band green light.

Preferably, the image sensor is an image sensor in combination with simultaneous lighting.

Preferably, the light source apparatus includes a normal light source device for generating normal light, and a narrow band light source device for generating the narrow band light. Furthermore, an image signal processor is supplied with the pixel signal by the image sensor, for generating a normal image of the object in case the normal light is used, and generating a special image of the object in case the narrow band light is used.

Also, an endoscope operating method is provided, and includes a step of emitting narrow band light of one or more components in field sequential lighting, for endoscopic imaging. An object in a body cavity illuminated with the narrow band light is imaged by use of an image sensor having plural pixels arranged on an imaging surface, to output a pixel signal, wherein the plural pixels include first and second pixels, and the first pixel has a lower spectral sensitivity than the second pixel. Gain correction of multiplying the pixel signal of the first pixel by a gain value is performed, so as to compensate for a difference in the spectral sensitivity of the first pixel from the second pixel.

Preferably, noise reduction of the pixel signal after the gain correction is performed according to the gain value.

Consequently, a difference in spectral sensitivity between pixels can be compensated for easily and appropriately, owing to operation of a gain corrector for pixel signals. Gain values of the gain correction for correcting pixels of an image sensor can be obtained with efficiency and simplicity.

BRIEF DESCRIPTION OF THE DRAWINGS

The above objects and advantages of the present invention will become more apparent from the following detailed description when read in connection with the accompanying drawings, in which:

FIG. 15 is an explanatory view in a plan, illustrating pixel signals after gain correction in imaging by using narrow band violet light;

FIG. 16 is an explanatory view in a plan, illustrating pixel signals after the gain correction in imaging by using narrow band green light;

FIG. 17 is an explanatory view in a plan, illustrating image data after synchronization processing;

DETAILED DESCRIPTION OF THE PREFERRED EMBODIMENT(S) OF THE PRESENT INVENTION

Figure 1:
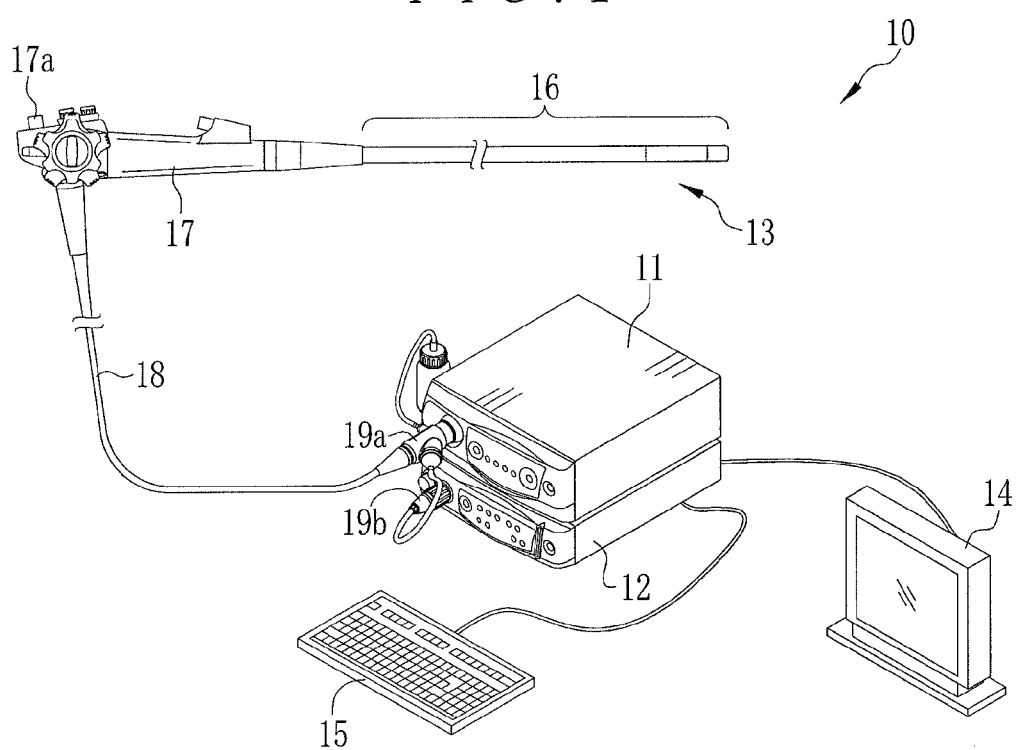
FIG. 1 is a perspective view illustrating an endoscope system.

In FIG. 1, an endoscope system 10 includes an electronic endoscope 13, a light source apparatus 11 and a processing apparatus 12. The endoscope 13 is connectable to the light source apparatus 11 and the processing apparatus 12 in a removable manner. The light source apparatus 11 generates light for supply to the endoscope 13. A tip of the endoscope 13 is entered in a body cavity of a patient, and images an object of interest in the body cavity. The processing apparatus 12 controls imaging of the endoscope 13, and processes an image signal from the endoscope 13 for image processing.

A display panel 14 and a user input interface 15 are connected to the processing apparatus 12. An example of the display panel 14 is a liquid crystal display panel or the like, and displays an image of an object of interest output by the processing apparatus 12. An example of the user input interface 15 is a keyboard, mouse or the like, and inputs information of various types to the processing apparatus 12.

The endoscope 13 includes an elongated tube 16, a grip handle 17, a universal cable 18, alight guide connector 19a and a signal connector 19b. The elongated tube 16 is a long tube and entered in a body cavity of a patient. The grip handle 17 is disposed at a proximal end of the elongated tube 16, and has a scope switch unit, steering wheels and the like. A mode selector 17a or selection switch is included in the scope switch unit for changing over an imaging mode.

The universal cable 18 extends from the grip handle 17. The light guide connector 19a and the signal connector 19b are disposed at a proximal end of the universal cable 18. The light guide connector 19a is coupled to the light source apparatus 11 in a removable manner. The signal connector 19b is coupled to the processing apparatus 12 in a removable manner.

There are two imaging modes in the endoscope system 10, including a normal imaging mode and a narrow band imaging mode. In the normal imaging mode, normal white light having a large wavelength range from blue to red is applied to an object of interest, to obtain a normal light image (normal image). In the narrow band imaging mode, narrow band violet light (Vn) and narrow band green light (Gn) as components of narrow wavelength ranges are applied to an object of interest, to obtain a special image.

The mode selector 17a described above is operable for selectively setting the normal imaging mode and the narrow band imaging mode. Note that other structures (not shown) can be used for changeover of the imaging modes, for example, a foot switch connected to the processing apparatus 12, a button in a front panel of the processing apparatus 12, the user input interface 15 or the like.

Figure 2:
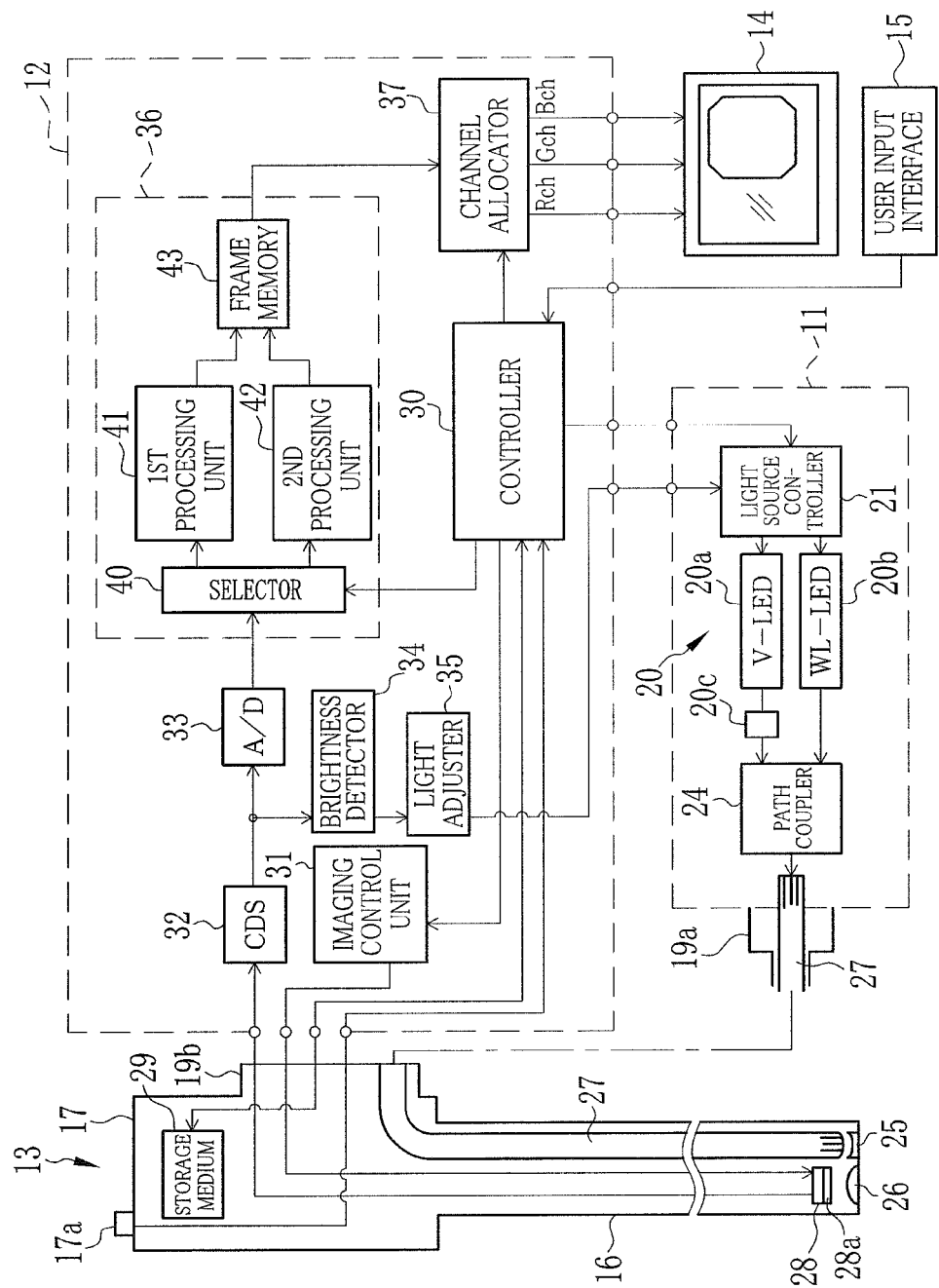
FIG. 2 is a block diagram schematically illustrating the endoscope system.

In FIG. 2, the light source apparatus 11 includes an LED light source 20, a light source controller 21 and a path coupler 24. The LED light source 20 includes a violet LED 20a (V-LED or violet light emitting diode, as narrow band light source device), a white LED 20b (WL-LED as normal light source device), and a violet narrow band filter 20c.

Figure 3:
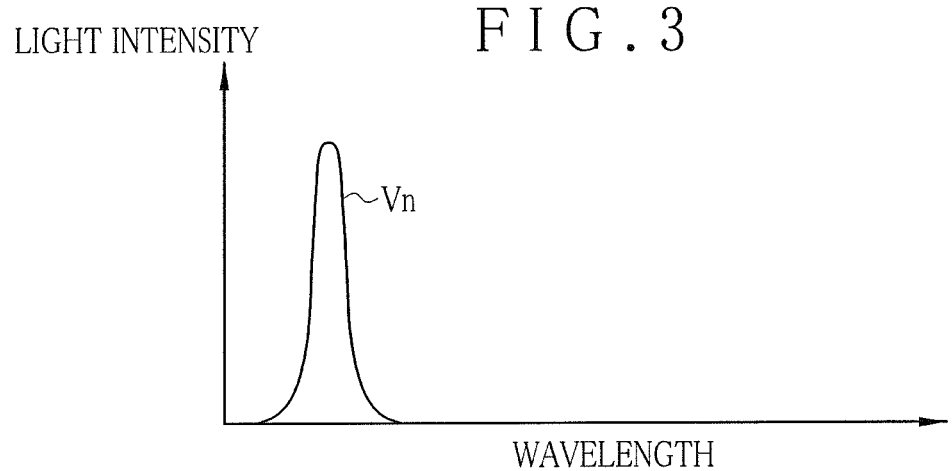
FIG. 3 is a graph illustrating a spectrum of narrow band violet light.
Figure 4:
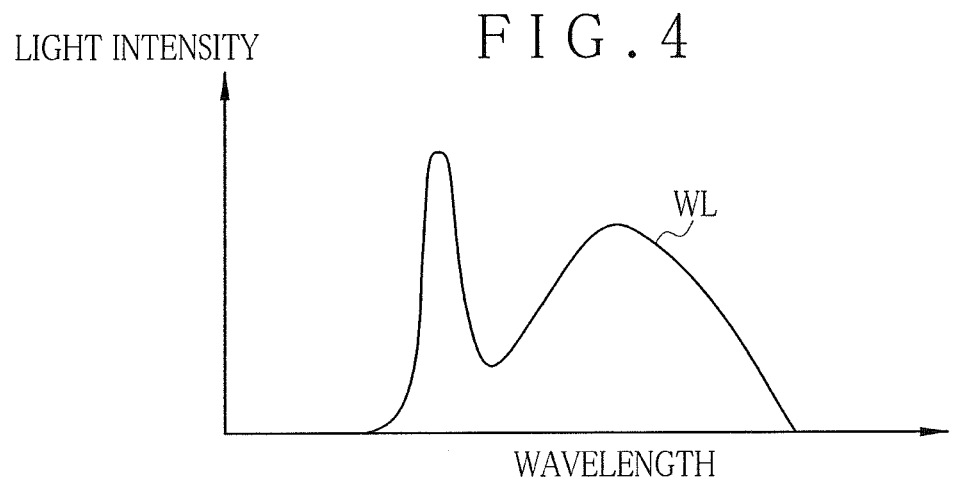
FIG. 4 is a graph illustrating a spectrum of normal white light.

The violet LED 20a emits violet light of a wavelength range of 380-440 nm. The violet narrow band filter 20c transmits light of only a wavelength range of 400-430 nm in the violet light from the violet LED 20a, and outputs narrow band violet light Vn of a wavelength range of 400-430 nm with a spectrum of light intensity of FIG. 3. The white LED 20b emits white light of a wide wavelength range with a spectrum of light intensity of FIG. 4. The light source controller 21 controls the violet and white LEDs 20a and 20b for light emission.

Figure 5:
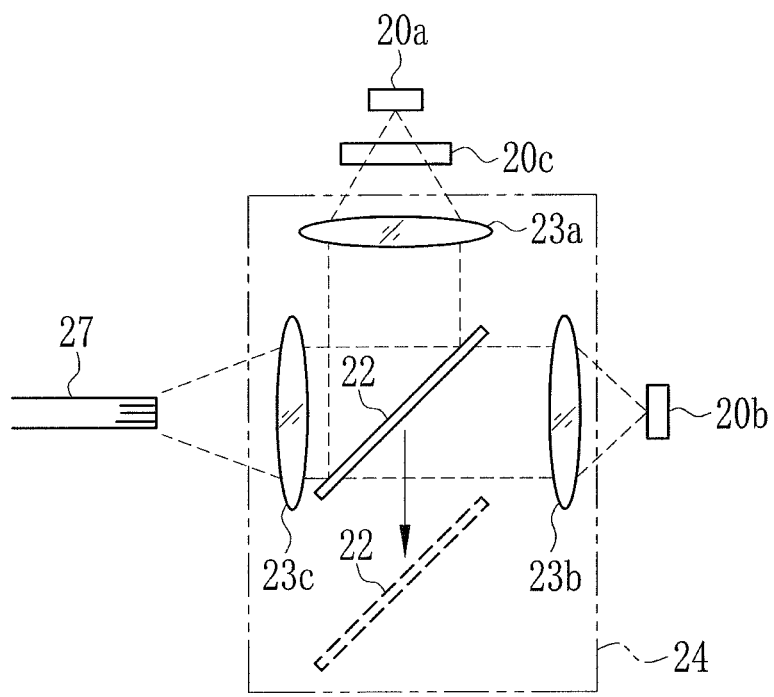
FIG. 5 is an explanatory view in a side elevation, illustrating a path coupler.

In FIG. 5, the path coupler 24 includes a dichroic mirror 22 (filter portion), a first lens 23a, a second lens 23b and a third lens 23c. The first and second lenses 23a and 23b are disposed downstream of respectively the violet and white LEDs 20a and 20b, and condense light from the violet and white LEDs 20a and 20b to output parallel light. The violet and white LEDs 20a and 20b are so disposed that their light paths extend perpendicularly to one another. The dichroic mirror 22 is positioned at an intersection point of the light paths.

Figure 6:
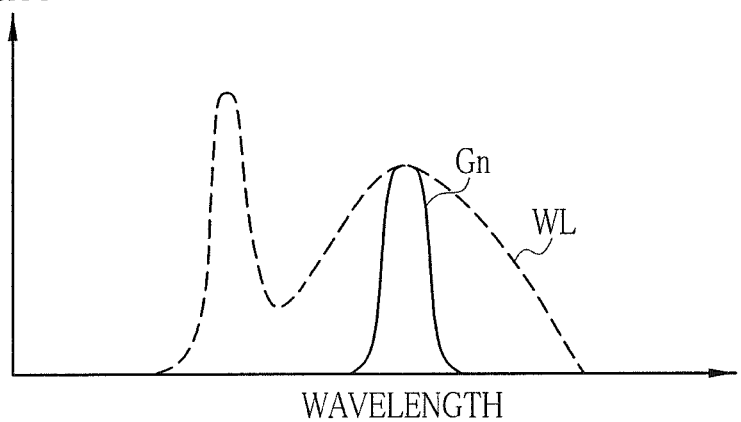
FIG. 6 is a graph illustrating a spectrum of narrow band green light.

The dichroic mirror 22 has a transmission characteristic of transmitting light of a wavelength range equal to or more than 530 nm and less than 550 nm, and reflects light of wavelengths less than 530 nm and equal to or more than 550 nm. The narrow band violet light Vn is reflected by the dichroic mirror 22 and condensed by the third lens 23c. In contrast, part of the white light WL is transmitted through the dichroic mirror 22 to become narrow band green light Gn of FIG. 6 with a wavelength range of 530-550 nm. The third lens 23c condenses the narrow band green light Gn.

In the narrow band imaging mode, the violet and white LEDs 20a and 20b are turned on alternately. The narrow band violet light Vn and narrow band green light Gn are condensed by the third lens 23c alternately, and enter a light guide device 27.

In the normal imaging mode, a mirror driver (not shown) shifts the dichroic mirror 22 out of a light path of the white LED 20b. The white light WL directly enters the third lens 23c and is supplied to the light guide device 27. As the dichroic mirror 22 in the normal imaging mode is set away, the narrow band violet light Vn does not enter the third lens 23c even though reflected by the dichroic mirror 22. The violet LED 20a may be turned on or off in the normal imaging mode.

A central wavelength of the narrow band violet light Vn is approximately 405 nm, so that its absorption coefficient of hemoglobin is high in a wavelength range of visible light. A central wavelength of the narrow band green light Gn is approximately 540 nm, so that its absorption coefficient of hemoglobin is high in a wavelength range of green light. Also, reflectance of the narrow band green light Gn in relation to mucosa is higher than that of the narrow band violet light Vn.

There are lighting windows and a viewing window disposed at a distal end of the elongated tube 16 of the endoscope 13. A lighting lens 25 is positioned in each of the lighting windows. An objective lens 26 is positioned in the viewing window. The light guide device 27 extends through the endoscope 13, and has a distal end opposed to the lighting lens 25. A proximal end of the light guide device 27 is disposed in the light guide connector 19a, and entered in the light source apparatus 11.

The lighting lens 25 condenses light exited from the light guide device 27 downstream of the light source apparatus 11, and applies the light to an object of interest in the body cavity. The objective lens 26 receives and condenses reflected light from the object of interest, such as body tissue, and forms an optical image. A multi-color image sensor 28 or image sensor of simultaneous lighting control (normal lighting with white light) is positioned at a point of focusing of the objective lens 26 for generating an image signal by imaging the object. A preferable example of the multi-color image sensor 28 is a CCD image sensor (charge coupled device image sensor).

Figure 7:
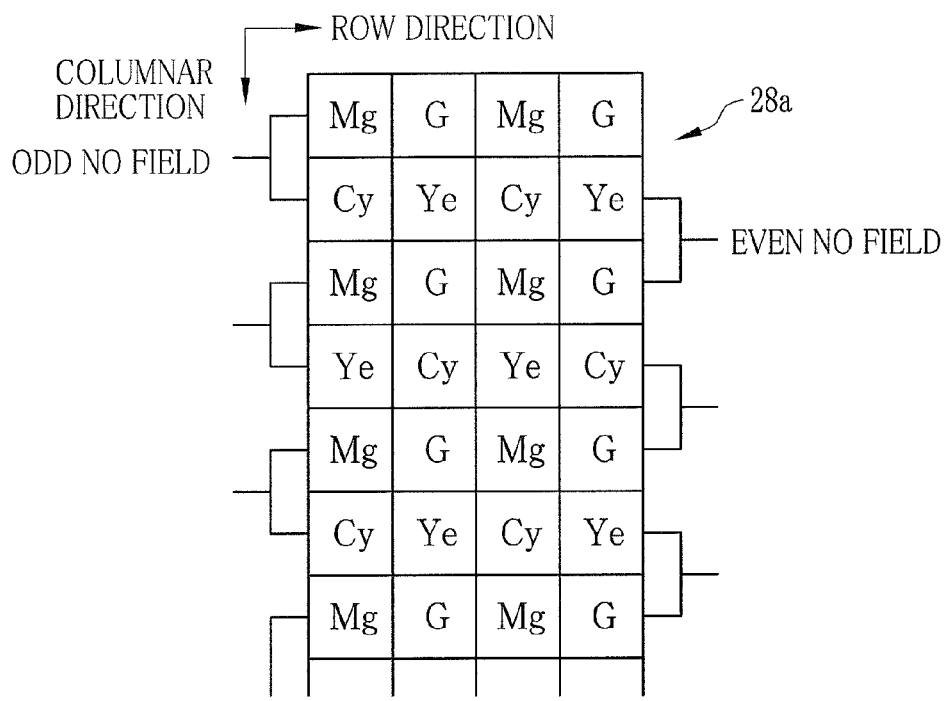
FIG. 7 is an explanatory view in a plan, illustrating a complementary color separation filter.

A complementary color separation filter 28a or multi-color separation filter is disposed on an imaging surface of the multi-color image sensor 28. In FIG. 7, the complementary color separation filter 28a includes magenta (Mg), green (G), cyan (Cy) and yellow (Y) color filter segments arranged at pixels. In short, the multi-color image sensor 28 has magenta, green, cyan and yellow pixels. Among those, magenta, cyan, magenta and yellow pixels are arranged cyclically in pixel columns of odd numbers. Green, yellow, green and cyan pixels are arranged cyclically in pixel columns of even numbers. Magenta and green pixels are arranged alternately in pixel rows of odd numbers. Cyan and yellow pixels are arranged alternately in pixel rows of even numbers. Arrangement of those color filters is referred to as line-sequential color difference arrangement or complementary interlace.

A flash memory or storage medium 29 as non-volatile memory is incorporated in the endoscope 13, and stores property information of the endoscope 13, for example, information of color filter arrangement of the image sensor, pixel number of its pixels and the like.

The processing apparatus 12 includes a controller 30, an imaging control unit 31, a correlation double sampler 32 (CDS), an A/D converter 33, a brightness detector 34, a light adjuster 35, an image signal processor 36 and a channel allocator 37.

The controller 30 controls various elements in the processing apparatus 12 and the light source apparatus 11. In response to connection of the endoscope 13 to the light source apparatus 11 and the processing apparatus 12, the controller 30 reads the property information from the storage medium 29. The imaging control unit 31 drives the multi-color image sensor 28 according to the property information.

The imaging control unit 31 drives the multi-color image sensor 28 according to an emission time point of the light source apparatus 11. In the normal imaging mode, the imaging control unit 31 drives the multi-color image sensor 28 in a method of field readout. In the narrow band imaging mode, the imaging control unit 31 drives the multi-color image sensor 28 in a method of progressive readout.

In the field readout, pixel signals of pixels of two pixel rows are mixed (added up) in relation to two pixels adjacent in a columnar direction at the time of readout in the odd number field and even number field. See FIG. 7. The mixture of the pixel signals is performed in a horizontal transfer path (not shown) in the CCD image sensor.

Figure 8:
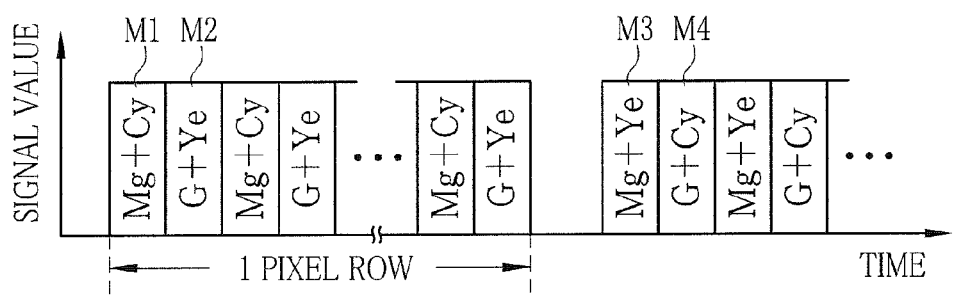
FIG. 8 is a timing chart illustrating an output signal from the image sensor in field readout.

According to the field readout, the multi-color image sensor 28 outputs first to fourth mixture pixel signals M1-M4 for each of the odd number field and even number field as illustrated in FIG. 8. The first mixture pixel signal M1 is a mixture pixel signal of a magenta pixel and a cyan pixel. The second mixture pixel signal M2 is a mixture pixel signal of a green pixel and a yellow pixel. The third mixture pixel signal M3 is a mixture pixel signal of a magenta pixel and a yellow pixel. The fourth mixture pixel signal M4 is a mixture pixel signal of a green pixel and a cyan pixel.

Figure 9:
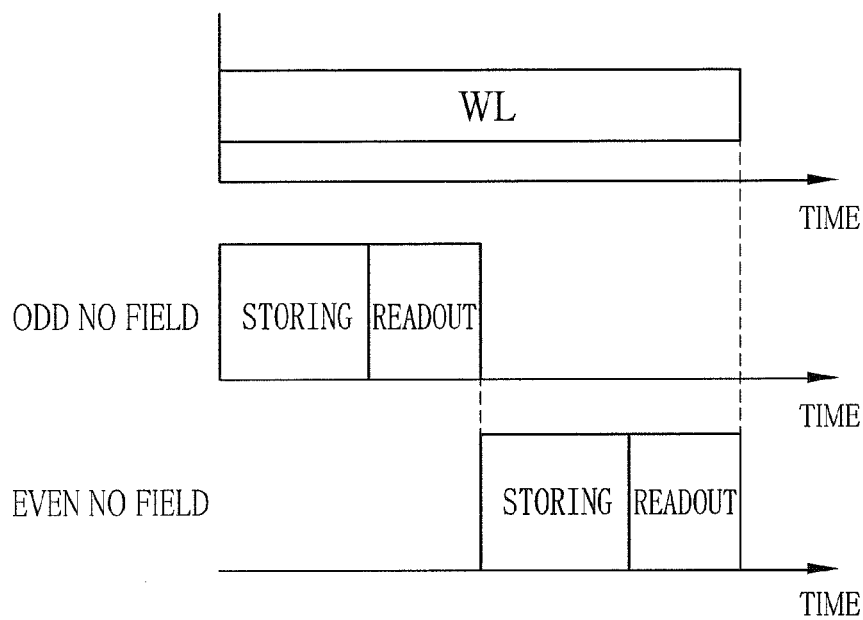
FIG. 9 is a timing chart illustrating a driving sequence of a light source apparatus and the image sensor in a normal imaging mode.

In the normal imaging mode, white light WL is emitted as illustrated in FIG. 9. Readout of the odd number field and even number field in the multi-color image sensor 28 is performed during the emission of the light. An image of one frame is produced from the odd number field and even number field of the readout.

Figure 10:
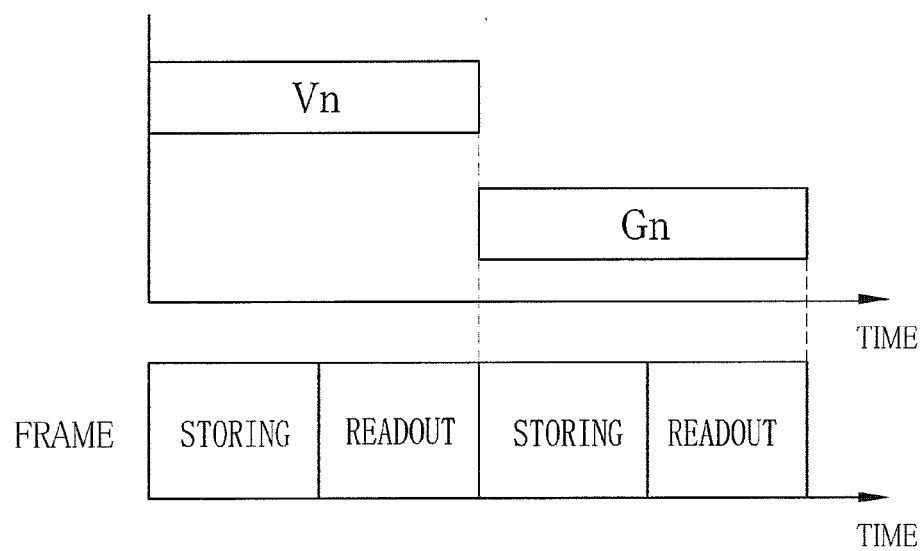
FIG. 10 is a timing chart illustrating a driving sequence of the light source apparatus and the image sensor in a narrow band imaging mode.

In the progressive readout, the multi-color image sensor 28 is driven sequentially by one pixel row, to read out magenta, green, cyan and yellow pixels discretely without mixing pixel signals. In the narrow band imaging mode, the narrow band violet light Vn and narrow band green light Gn are emitted alternately. See FIG. 10. One frame is read out from the multi-color image sensor 28 in each one period of lighting, to produce an image of one frame.

Signals from the multi-color image sensor 28 are input to the CDS 32. The CDS 32 eliminates noise components from the signals due to the CCD image sensor by performing the correlation double sampling. The signal after the noise elimination in the CDS 32 is supplied to the A/D converter 33, and also output to the brightness detector 34. The A/D converter 33 converts the signal into a digital signal, which is supplied to the image signal processor 36.

The brightness detector 34 detects brightness of an object of interest according to a signal input by the CDS 32, namely an average brightness of the input signal. The light adjuster 35 produces an adjustment signal by subtraction of the brightness signal from the brightness detector 34 from a reference brightness or target value of the light adjustment. The light source controller 21 is supplied with the adjustment signal. The light source controller 21 controls light intensity of the plural LEDs in the LED light source 20 to regulate a light amount of the light so as to obtain the reference brightness.

Also, the controller 30 receives a mode selection signal input by operation of the mode selector 17a of the endoscope 13, and controls elements in the processing apparatus 12 and the light source controller 21 according to one of the imaging modes specified by the mode selection signal.

At the start of the imaging, the controller 30 performs motion imaging of an object in a body cavity by repeatedly driving the multi-color image sensor 28 and the LED light source 20 controlled by the imaging control unit 31 and the light source controller 21. In the motion imaging, the controller 30 receives a mode selection signal from the mode selector 17a, and changes over the lighting control of the light source apparatus 11 and the method of readout of the multi-color image sensor 28.

The image signal processor 36 includes a selector 40, a first signal processing unit 41 for simultaneous lighting control (normal lighting with white light), a second signal processing unit 42 for field sequential lighting control, and a frame memory 43. The selector 40 is controlled by the controller 30, and selects the first or second signal processing unit 41 or 42 according to the imaging mode. In the normal imaging mode, the first signal processing unit 41 is selected. In the narrow band imaging mode, the second signal processing unit 42 is selected.

Figure 11:
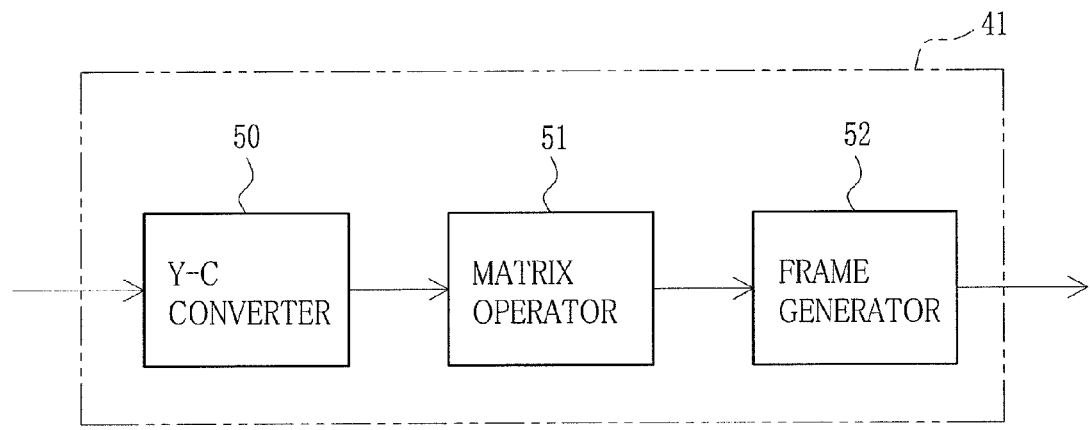
FIG. 11 is a block diagram schematically illustrating an image signal processor in combination with simultaneous lighting.

In FIG. 11, the first signal processing unit 41 includes a Y-C converter 50, a matrix operator 51 and a frame generator 52. The first to fourth mixture pixel signals M1-M4 are sequentially input to the Y-C converter 50 by the multi-color image sensor 28 and through the CDS 32 and the A/D converter 33.

The Y-C converter 50 operates for Y-C conversion according to well-known arithmetic operations for use in the line-sequential color difference arrangement or complementary interlace, and produces a luminance signal Y and chrominance signals Cr and Cb. Those are determined by addition or subtraction between the first and second mixture pixel signals M1 and M2 adjacent with one another in the row direction, and by addition or subtraction between the third and fourth mixture pixel signals M3 and M4 adjacent with one another in the row direction.

The matrix operator 51 performs a predetermined matrix operation for the luminance signal Y and chrominance signals Cr and Cb from the Y-C converter 50, and produces RGB signals. The Y-C converter 50 and the matrix operator 51 operate for each of the odd number field and even number field in relation to the Y-C conversion and the matrix operation.

The frame generator 52 generates image data of one frame according to RGB signals obtained for each one of the odd number field and even number field. To this end, interpolation is performed by use of plural adjacent pixels (for example, eight pixels next to a target pixel) for producing RGB signals according to pixels of image data of one frame. The frame generator 52 stores the image data to the frame memory 43 at each time of producing the image data of one frame.

Figure 12:
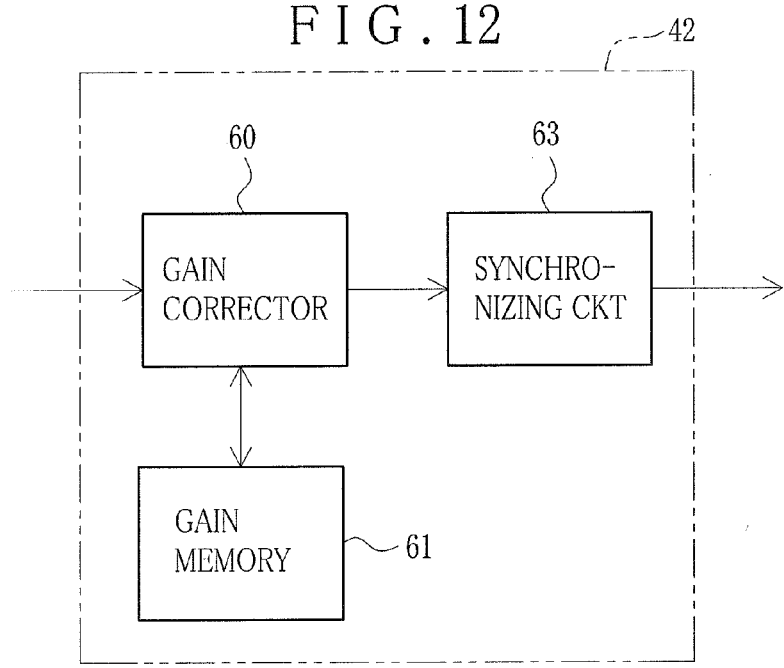
FIG. 12 is a block diagram schematically illustrating an image signal processor in combination with field sequential lighting.

In FIG. 12, the second signal processing unit 42 includes a gain corrector 60, a gain memory 61 or gain storage medium, and a synchronizing circuit 63 for synchronization processing. The gain corrector 60 is supplied with pixel signals of magenta, cyan, green and yellow pixels discretely by the multi-color image sensor 28 through the CDS 32 and the A/D converter 33. Let $P_{1M}$, $P_{1C}$, $P_{1G}$ and $P_{1Y}$ be pixel signals of the magenta, cyan, green and yellow pixels according to lighting with the narrow band violet light Vn. Let $P_{2M}$, $P_{2C}$, $P_{2G}$ and $P_{2Y}$ be pixel signals of the magenta, cyan, green and yellow pixels according to lighting with the narrow band green light Gn.

Figure 13:
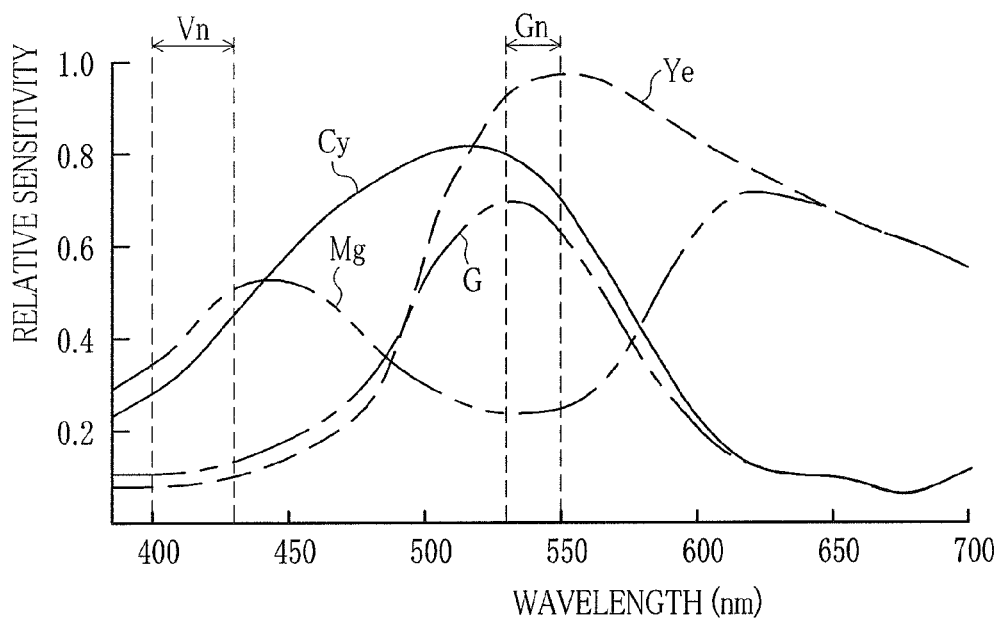
FIG. 13 is a graph illustrating a spectrum of spectral sensitivity of pixels.

The gain corrector 60 corrects pixel signals of pixels of low sensitivity in the gain correction by use of the gains stored in the gain memory 61, to compensate for differences in spectral sensitivity of the pixels in relation to the narrow band violet light Vn and narrow band green light Gn. As illustrated in FIG. 13 for spectra of the spectral sensitivity of pixels of the multi-color image sensor 28, the magenta pixels are the most sensitive to the narrow band violet light Vn. The yellow pixels are the most sensitive to the narrow band green light Gn. Consequently, the gain correction is performed for pixel signals $P_{1C}$, $P_{1G}$ and $P_{1Y}$ of the cyan, green and yellow pixels in the emission of the narrow band violet light Vn. Also, the gain correction is performed for pixel signals $P_{2M}$, $P_{2C}$ and $P_{2G}$ of the magenta, cyan and green pixels in the emission of the narrow band green light Gn.

The gain memory 61 stores information of gain values $K_{1i}$ and $K_{2i}$. The gain value $K_{1i}$ is used for gain correction of a pixel signal $P_{1i}$ (i=C, G or Y) upon lighting of the narrow band violet light Vn. The gain value $K_{2i}$ is used for gain correction of a pixel signal $P_{2i}$ (i=M, C or G) upon lighting of the narrow band green light Gn.

In general, the pixel signal $P_{ki}$ is proportional to a value of integration of a product of multiplication of a spectrum $I_k(\lambda)$ of light intensity of light of illumination, a spectrum $S_i(\lambda)$ and a spectrum $R(\lambda)$, from minimum wavelength λmin to maximum wavelength λmax of the spectrum $I_k(\lambda)$ of the light intensity. See the mathematical relationship (2). Note that the spectrum $S_i(\lambda)$ of spectral sensitivity of the pixel is based upon a photo diode, color filter segment, optics and the like.

$$P_{ki} \propto \int_{\lambda_{min}}^{\lambda_{max}} I_k(\lambda) \cdot S_k(\lambda) \cdot R(\lambda) d\lambda \quad (2)$$

In the mathematical relationship, k=1 or 2, and 1 denotes the narrow band violet light Vn, and 2 denotes the narrow band green light Gn. $I_1(\lambda)$ is a spectrum of light intensity of narrow band violet light Vn. $I_2(\lambda)$ is a spectrum of light intensity of narrow band green light Gn. $S_i(\lambda)$ is a spectrum of spectral sensitivity of each pixel. $R(\lambda)$ is a spectrum of spectral reflection of body tissue or object of interest.

Figure 14:
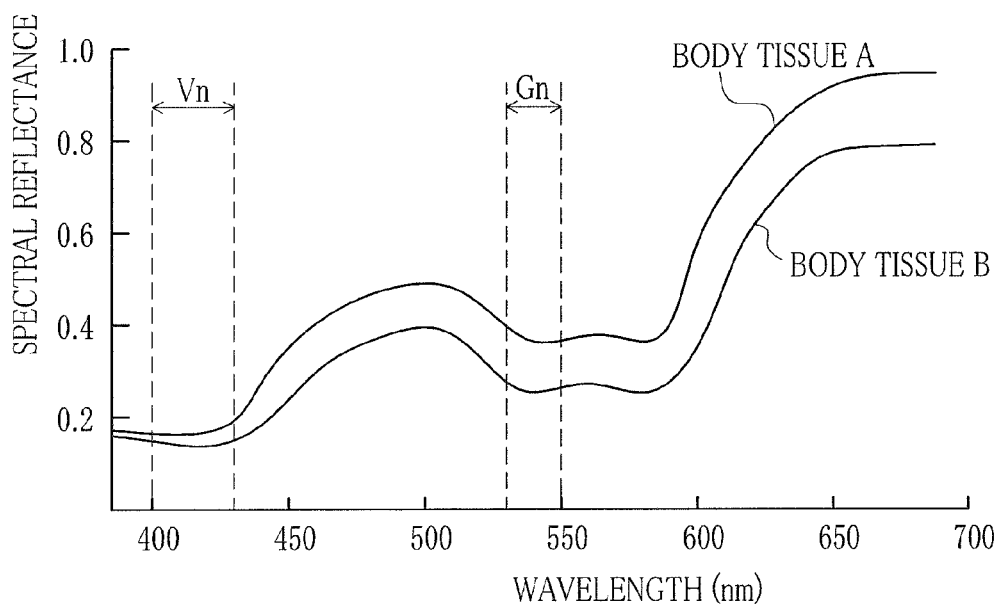
FIG. 14 is a graph illustrating a spectrum of spectral reflection of body tissue.

In FIG. 14, spectra of spectral reflection of two samples A and B of body tissue or mucosa are illustrated. The spectra change according to surfaces of the body tissue. However, wavelength ranges of the narrow band violet light Vn and narrow band green light Gn have such a small width as 30 nm or lower, so that the spectrum $R(\lambda)$ of the spectral reflection is nearly constant in each wavelength range without remarkable changes. Thus, it is possible to neglect dependency of $R(\lambda)$ to the wavelength and to replace $R(\lambda)$ in the mathematical relationship (2) with Rk, which is an average of spectral reflectance in each wavelength range. See the mathematical relationship (3).

$$P_{ki} \propto R_k \int_{\lambda_{min}}^{\lambda_{max}} I_k(\lambda) \cdot S_i(\lambda) d\lambda \quad (3)$$

The gain values $K_{1i}$ (i=C, G or Y) and $K_{2i}$ (i=M, C or G) stored in the gain memory 61 are obtained according to equations (4) and (5).

$$K_{1i} = P_{1M}/P_{1i} \quad (4)$$

$$K_{2i} = P_{2Y}/P_{2i} \quad (5)$$

Rewriting the equations (4) and (5) by use of the mathematical relationship (3) results in cancellation of Rk. Therefore, it is found that the gain values $K_{1i}$ and $K_{2i}$ are constant without dependency upon the spectral reflectance of body tissue. It is possible to determine the gain values $K_{1i}$ and $K_{2i}$ according to the spectrum $I_k(\lambda)$ of the light intensity of the narrow band violet light Vn and narrow band green light Gn and the spectrum $S_i(\lambda)$ of spectral sensitivity of the pixel.

In the embodiment, the gain values $K_{1i}$ and $K_{2i}$ can be acquired by use of the mathematical relationships (3)-(5) theoretically. However, pixel signals $P_{ki}$ can be actually obtained from imaging irradiated white portions with the narrow band violet light Vn and narrow band green light Gn on a white test object without color unevenness. The gain values $K_{1i}$ and $K_{2i}$ can be obtained form the equations (4) and (5) according to the obtained pixel signals $P_{ki}$.

The gain corrector 60 performs the gain correction according to the equations (6) and (7) for the pixel signals (i=C, G or Y) and $P_{2i}$ (i=M, C or G) obtained by imaging in the narrow band imaging mode.

$$P_{1i}' = P_{1i} \times K_{1i} \quad (6)$$

$$P_{2i}' = P_{2i} \times K_{2i} \quad (7)$$

After the gain correction, the pixel signal $P_{11}$ obtained by lighting with the narrow band violet light Vn is converted as illustrated in FIG. 15. The pixel signal $P_2$±obtained by lighting with the narrow band green light Gn is converted as illustrated in FIG. 16.

A signal level of a pixel signal $P_{1i}'$ after the gain correction (i=C, G or Y) is near to that of a pixel signal $P_{1M}$ of the magenta pixel of high sensitivity. Thus, a difference in spectral sensitivity is compensated for. Similarly, a signal level of a pixel signal $P_{2i}'$ after the gain correction (i=M, C or G) is near to that of a pixel signal $P_{2Y}$ of the yellow pixel of high sensitivity. Thus, a difference in spectral sensitivity is compensated for. Now signs of pixel signals $Q_{1i}$ and $Q_{2i}$ (i=M, C, G or Y) are used for a combination of the pixel signal $P_{1i}'$ (i=C, G or Y) and the pixel signal $P_{2i}'$ (i=M, C or G) after the gain correction, and the pixel signals $P_{1M}$ and $P_{2Y}$ of high sensitivity without the gain correction.

Then the synchronizing circuit 63 synchronizes the pixel signals $P_{1i}'$, and $P_{2i}'$ after the gain correction and corresponding to the narrow band violet light Vn and narrow band green light Gn, to produce image data of one frame, which is written to the frame memory 43. In FIG. 17, the pixel signals $Q_{1i}$ and $Q_{2i}$ are allocated to pixels of the image data. As a result, no interpolation by use of peripheral pixels is required, so that spatial resolution at such a high level as imaging with a monochromatic image sensor can be obtained.

The channel allocator 37 allocates image data from the frame memory 43 to each one of the channels of the display panel 14 for displaying an image of the image data. In the normal imaging mode, the RGB signals of pixels of the image data are allocated to the R, G and B channels of the display panel 14 for displaying a normal image. In the narrow band imaging mode, a pixel signal $Q_{1i}$ of a pixel in the image data is allocated to the G channel, and a pixel signal $Q_{2i}$ of a pixel in the image data is allocated to the B channel, for displaying a special image. Note that a signal level of the pixel signal $Q_{1i}$ is lower than that of the pixel signal $Q_{2i}$, so the pixel signal $Q_{1i}$ can be allocated to the R channel in addition to the G channel.

Figure 18:
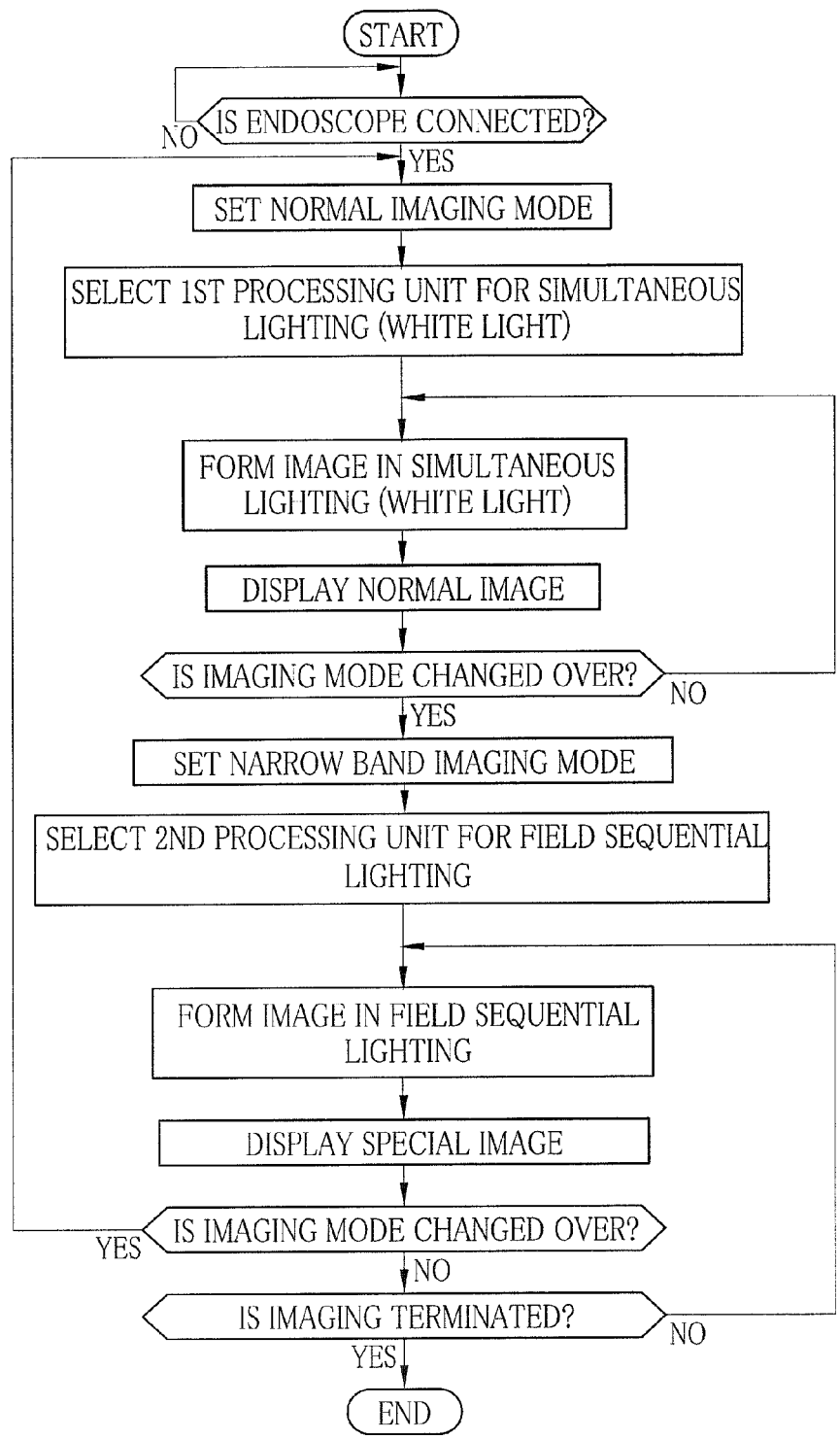
FIG. 18 is a flow chart illustrating operation of the endoscope system.

The operation of the endoscope system 10 is described now by referring to the flow in FIG. 18. A physician or operator connectively couples the endoscope 13 to the light source apparatus 11 and the processing apparatus 12. The controller 30 in the processing apparatus 12 sets the normal imaging mode in the light source apparatus 11 and the processing apparatus 12, and causes the selector 40 in the image signal processor 36 to select the first signal processing unit 41.

In the normal imaging mode, the dichroic mirror 22 (filter portion) in the path coupler 24 of the light source apparatus 11 is shifted away. The white LED 20b (normal light source device) is turned on to generate normal white light WL, which is supplied to the light guide device 27 in the endoscope 13. The multi-color image sensor 28 is driven in the method of field readout, and output the first to fourth mixture pixel signals M1-M4. Those signals are converted for the Y-C conversion by the first signal processing unit 41, and converted into RGB signals, to drive the display panel 14 for displaying through the channel allocator 37. A normal image is displayed on the display panel 14 as a result of imaging in the simultaneous lighting of normal light.

The physician or operator enters the elongated tube 16 of the endoscope 13 in a body cavity for endoscopic imaging. In case he or she wishes to observe a condition of surface blood vessels of body tissue or an object of interest, the mode selector 17a is operated for changeover. A mode selection signal from the mode selector 17a is received by the controller 30, which sets the light source apparatus 11 and the processing apparatus 12 in the narrow band imaging mode.

In the narrow band imaging mode, the second signal processing unit 42 is selected by the selector 40. Also, a lighting control of the light source apparatus 11 is changed. The dichroic mirror 22 in the path coupler 24 is set at an intersection point of light paths of the violet and white LEDs 20a and 20b. The violet and white LEDs 20a and 20b are turned on alternately. Thus, the narrow band violet light Vn and narrow band green light Gn are emitted alternately to travel through the light guide device 27 in the endoscope 13. The multi-color image sensor 28 in the endoscope 13 is driven in the method of progressive readout, to output pixel signals $P_{1i}$ and $P_{2i}$. The second signal processing unit 42 corrects the pixel signals $P_{1i}$ and $P_{2i}$ in the gain correction, and synchronized, so as to drive the display panel 14 for display by use of the channel allocator 37. A special image is displayed on the display panel 14 as an image according to lighting with narrow band light and in the field sequential lighting.

The narrow band violet light Vn can reach a first depth of penetration from a surface of body tissue. An area in a special image according to the narrow band violet light Vn comes to contain partial images of surface blood vessels of the first depth being small. The narrow band green light Gn can reach a second depth of penetration longer than the first depth from the surface of body tissue. An area in the special image according to the narrow band green light Gn comes to contain partial images of deep blood vessels or intermediate deep blood vessels of the second depth.

Displaying the special image is repeated until the mode selector 17a is operated or until the user input interface 15 is manipulated for terminating the imaging. Upon operating the mode selector 17a, the normal imaging mode is set again. Upon operating the user input interface 15 for termination, the imaging is terminated.

Second Preferred Embodiment

Figure 19:
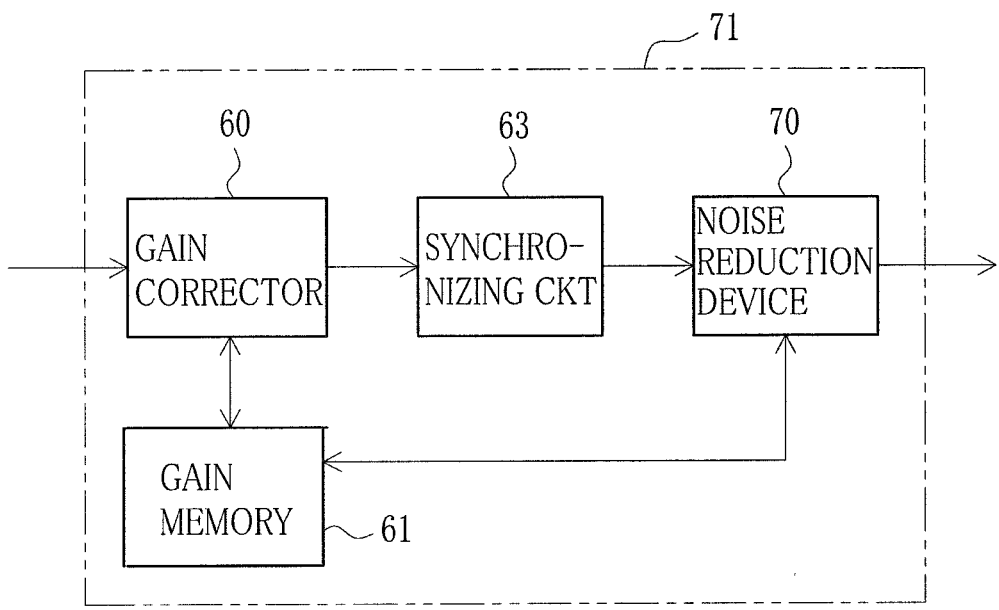
FIG. 19 is a block diagram schematically illustrating another preferred image signal processor.

In FIG. 19, a second preferred endoscope system includes a signal processing unit 71 for field sequential lighting control, having a noise reduction device 70. For the remaining elements other than the signal processing unit 71, the endoscope system 10 of the first embodiment is repeated.

Figure 20:
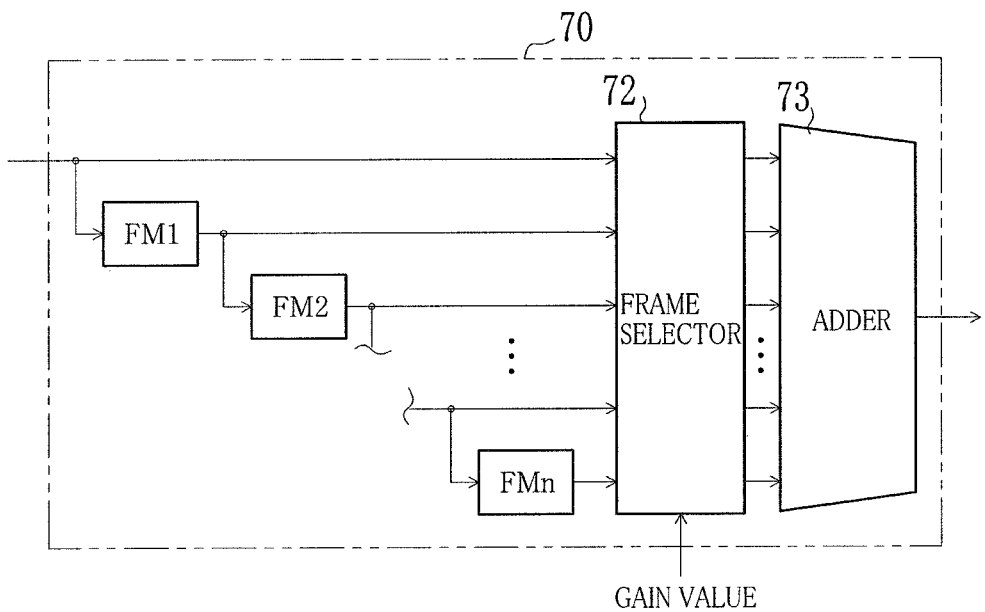
FIG. 20 is a block diagram schematically illustrating a noise reduction device.

The noise reduction device 70 is disposed downstream of the synchronizing circuit 63. In FIG. 20, the noise reduction device 70 includes plural frame memories FM1-FMn, a frame selector 72 and an adder 73. Image data output by the synchronizing circuit 63 is delayed by one period of a frame, and stored to the frame memories FM1-FMn sequentially.

The frame selector 72 selects m frame memories FM1-FMm among the frame memories FM1-FMn (where m is equal to or smaller than n) according to the gain value for the pixel signals $Q_{1i}$ and $Q_{2i}$ in the image data. In short, the frame selector 72 increases the number m for the selection according to highness of the gain value. For example, the frame selector 72 evaluates the gain value in four grades, and changes the number m stepwise for the selection. Assuming that the gain value is "1", namely for the pixel signals $Q_{1M}$ and $Q_{2Y}$ without gain correction, the frame selector 72 sets "0" for the number m. No frame memory is selected.

The adder 73 receives image data from the frame memory FM1-FMm selected by the frame selector 72, and adds and averages the pixel signals $Q_{1i}$ and $Q_{2i}$ for each of the pixels to acquire an arithmetic mean. Effect of reducing noise becomes high according to the highness of the number of the frames of the acquirement of an arithmetic mean. Thus, the number of the frames for the acquirement of an arithmetic mean is increased according to highness of a gain value of a pixel signal. This is because a level of a pixel signal before the gain correction is low in case the gain value of the pixel signal is high, so that a ratio of its noise component in the pixel signal is high.

It is possible in the second embodiment to reduce the noise due to the gain correction as well as the higher spatial resolution by use of the gain correction in the narrow band imaging mode.

Note that time resolution of the noise reduction device 70 in the embodiment is low for the reason of averaging the pixel signals with time by way of an arithmetic mean. In consideration of this, it is possible to use another noise reduction unit in which pixel signals are averaged in a spatial manner by way of an arithmetic mean within image data of one frame, in place of the noise reduction device 70.

Figure 21:
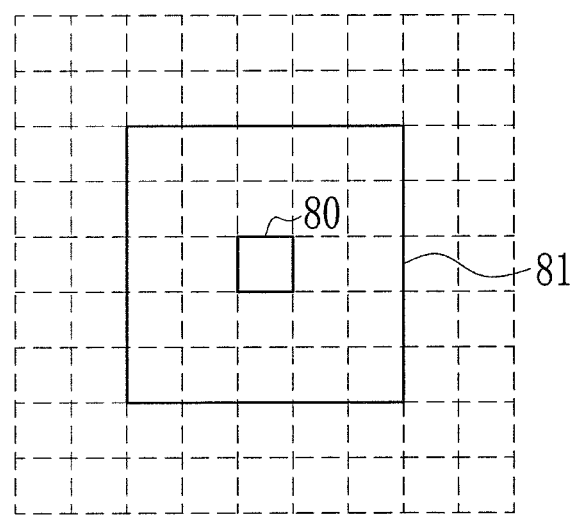
FIG. 21 is an explanatory view in a plan, illustrating pixel arrangement according to another preferred noise reduction.

In FIG. 21, the noise reduction device of this feature specifies a pixel area 81 to contain a pixel 80 in association with the pixel signal $Q_{ki}$. An arithmetic mean of the pixel signal $Q_{ki}$ within the pixel area 81 is obtained and used as a pixel signal for the pixel 80. To this end, a size of the pixel area 81 (number of pixel signals for the arithmetic mean) is enlarged according to highness of the gain signal from the pixel signal $Q_{ki}$ for the noise reduction. Note that a shape of the pixel area 81 can be different from the rectangular quadrilateral, for example, a cross shape and the like.

Figure 22:
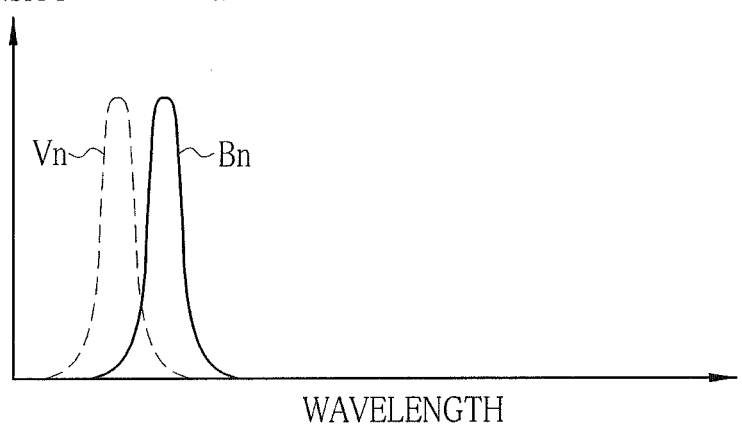
FIG. 22 is a graph illustrating a spectrum of narrow band blue light.

In the above embodiments, the violet and white LEDs 20a and 20b are used in the LED light source 20. However, a blue LED of FIG. 22 can be used in place of the violet LED 20a for generating narrow band blue light Bn having a longer wavelength than the narrow band violet light Vn. In combination, a blue narrow band filter is used in place of the violet narrow band filter 20c. A central wavelength of the narrow band blue light Bn is approximately 410-420 nm, preferably 415 nm.

Furthermore, three or more LEDs of different wavelength ranges, for example, blue, green and red, can be used in place of the violet and white LEDs 20a and 20b. It is possible to generate normal white light by turning on the LEDs simultaneously, and generate two components of narrow band light by turning on two selected LEDs among all of the LEDs.

Also, it is possible in the narrow band imaging mode to apply only one component of narrow band light to an object of interest, for example, narrow band violet light Vn. A width of a wavelength range of each component of narrow band light can be equal to or less than 30 nm, with which dependency of a spectrum of spectral reflection of an object of interest to the wavelength is negligible.

In the above embodiments, the pixel signals of the imaging are corrected by the gain correction in relation to both of the narrow band violet light Vn and narrow band green light Gn. However, it is possible to perform the gain correction of a pixel signal in imaging by using a first one of the components of the narrow band light, but not to correct a pixel signal in imaging by using a remaining one of the components of the narrow band light.

In the above embodiments, the multi-color image sensor 28 in the normal imaging mode is driven in the method of the field readout. However, the multi-color image sensor 28 can be driven in the method of the progressive readout. In the above embodiments, filter arrangement of the complementary color separation filter 28a or multi-color separation filter is line-sequential color difference arrangement or complementary interlace. However, other filter arrangements of the complementary color separation filter 28a can be used in compliance with the method of readout. In the above embodiment, the multi-color image sensor 28 is a type having the complementary color separation filter 28a of at least yellow, magenta and cyan colors. However, the multi-color image sensor 28 can be a type having a three primary color separation filter of blue, green and red colors.

Also, the imaging control unit 31, the CDS 32 and the A/D converter 33, although disposed in the processing apparatus 12 in the above embodiments, may be incorporated in the endoscope 13.

In the above embodiments, the gain corrector 60 corrects the pixel signals of the digital form output by the A/D converter 33 for the gain correction. However, it is possible in the gain correction to correct the pixel signals of an analog form upstream of the A/D converter 33.

Furthermore, an image sensor according to the invention can be a CMOS image sensor or the like. The CMOS image sensor includes a semiconductor substrate, on which it is possible to mount the imaging control unit 31, the CDS 32, the A/D converter 33 and the like.

In the above embodiments, the light source apparatus 11 has the LED light source 20. However, laser diodes (LD) or the like can be incorporated in the light source apparatus 11 instead of the LEDs of the LED light source 20.

In the above embodiments, the processing apparatus 12 is separate from the light source apparatus 11. However, a composite apparatus inclusive of components of the light source apparatus 11 and the processing apparatus 12 can be used. Also, a component of the light source apparatus 11 can be incorporated in the endoscope 13.

The gain memory 61 is caused initially to store the gain values at the time of factory shipment of the processing apparatus 12. However, it is possible experimentally to obtain a gain value at the time of maintenance or other condition setting of the endoscope system 10, to write the gain value to the gain memory 61. In short, color balance of the endoscope system 10 can be calibrated by use of the feature of the invention.

In the gain correction of the above embodiments, the pixel signal of the pixel of one color (magenta or yellow) with the highest sensitivity among the pixels of the four colors (cyan, magenta, yellow and green) is used without correction. The pixel signals of the pixels of the three colors with the lower sensitivity are corrected by the gain correction. However, pixel signals of pixels of two colors with higher sensitivity can be used without correction, and pixel signals of pixels of two colors with the lower sensitivity can be corrected by the gain correction. Furthermore, pixel signals of pixels of three colors with higher sensitivity can be used without correction, and a pixel signal of a pixel of one color with the lowest sensitivity can be corrected by the gain correction.

To this end, the technically known characteristics illustrated in FIG. 13 are utilized, in which a sequence of sensitivity of pixels to the narrow band violet light Vn is magenta, cyan, green and yellow, and a sequence of sensitivity of pixels to the narrow band green light Gn is yellow, cyan, green and magenta.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
   a light source apparatus for emitting first and second narrow band illumination light in field sequential lighting, for endoscopic imaging;
   a multi-color image sensor, having plural pixels arranged on an imaging surface, for imaging reflected light from an object in a body cavity illuminated with said first and second narrow band illumination light, to output a pixel signal, wherein said plural pixels include first and second pixels that are different in color, said first pixel has a lower spectral sensitivity than said second pixel to said first narrow band illumination light, and said second pixel has a lower spectral sensitivity than said first pixel to said second narrow band illumination light;
   a gain corrector, supplied with said pixel signal by said image sensor, for performing first gain correction of multiplying said pixel signal of said first pixel by a first gain value, so as to compensate for a difference in said spectral sensitivity to said first narrow band illumination light between said first pixel and said second pixel due to said color difference, and for performing second gain correction of multiplying said pixel signal of said second pixel by a second gain value to compensate for a difference in said spectral sensitivity to said second narrow band illumination light between said first pixel and said second pixel due to said color difference, wherein said first gain value and second gain value are determined according to a spectrum of light intensity of said first and second narrow band illumination light and a spectrum of spectral sensitivity of said first and second pixels, and are constant without dependency upon the spectral reflectance of said body tissue.

2. An endoscope system as defined in claim 1, wherein a wavelength range of said narrow band light has a width equal to or less than 30 nm.

3. An endoscope system as defined in claim 1, further comprising a noise reduction device for performing noise reduction of said pixel signal after said gain correction according to said gain value.

4. An endoscope system as defined in claim 3, wherein said noise reduction device obtains an arithmetic mean of said pixel signal of a plurality of frames formed with a time difference to perform said noise reduction, and increases a frame number of said frames for use in obtaining said arithmetic mean according to highness of said gain value.

5. An endoscope system as defined in claim 3, wherein said noise reduction device obtains an arithmetic mean of said pixel signal included in image data of one frame to perform said noise reduction, and increases a signal number of said pixel signal for use in obtaining said arithmetic mean according to highness of said gain value.

6. An endoscope system as defined in claim 1, further comprising a synchronizing circuit for synchronizing said pixel signal after said gain correction, to produce image data.

7. An endoscope system as defined in claim 1, wherein said narrow band light is narrow band violet light and narrow band green light.

8. An endoscope system as defined in claim 1, wherein said image sensor includes color filter segments of cyan, magenta, yellow and green colors disposed on said imaging surface, and said pixels are pixels of said cyan, magenta, yellow and green colors.

9. An endoscope system as defined in claim 8, wherein said first pixel is pixels of said cyan, yellow and green colors in imaging by using narrow band violet light, and is pixels of said cyan, magenta and green colors in imaging by using narrow band green light.

10. An endoscope system as defined in claim 1, wherein said image sensor is an image sensor in combination with simultaneous lighting.

11. An endoscope system as defined in claim 1, wherein said light source apparatus includes a normal light source device for generating normal light, and a narrow band light source device for generating said narrow band light;

further comprising an image signal processor, supplied with said pixel signal by said image sensor, for generating a normal image of said object in case said normal light is used, and generating a special image of said object in case said narrow band light is used.

12. An endoscope system as defined in claim 1, further comprising a channel allocator for allocating a combination of said pixel signal of said first pixel after said first gain correction and said pixel signal of said second pixel without said first gain correction to one channel of a display, and allocating a combination of said pixel signal of said second pixel after said second gain correction and said pixel signal of said first pixel without said second gain correction to another channel of said display.

13. An endoscope operating method comprising steps of:
emitting first and second narrow band illumination light in field sequential lighting, for endoscopic imaging;
imaging reflected light from an object in a body cavity illuminated with said first and second narrow band illumination light by use of a multi-color image sensor having plural pixels arranged on an imaging surface, to output a pixel signal, wherein said plural pixels include first and second pixels that are different in color, said first pixel has a lower spectral sensitivity than said second pixel to said first narrow band illumination light, and said second pixel has a lower spectral sensitivity than said first pixel to said second narrow band illumination light;
performing first gain correction of multiplying said pixel signal of said first pixel by a first gain value, so as to compensate for a difference in said spectral sensitivity to said first narrow band illumination light between said first pixel and said second pixel due to said color difference, and for performing second gain correction of multiplying said pixel signal of said second pixel by a second gain value to compensate for a difference in said spectral sensitivity to said second narrow band illumination light between said first pixel and said second pixel due to said color difference,
wherein said first gain value and second gain value are determined according to a spectrum of light intensity of said first and second narrow band illumination light and a spectrum of spectral sensitivity of said first and second pixels, and are constant without dependency upon the spectral reflectance of said body tissue.

14. An endoscope operating method as defined in claim 13, wherein noise reduction of said pixel signal after said gain correction is performed according to said gain value.

* * * * *